United States Patent [19]
Lazarovits et al.

[11] Patent Number: 6,099,838
[45] Date of Patent: Aug. 8, 2000

[54] PHARMACEUTICAL COMPOSITIONS COMPRISING ANTI-CD45RB ANTIBODIES FOR THE INHIBITION OF T-CELL MEDIATED IMMUNE RESPONSES

[75] Inventors: Andrew I. Lazarovits, London; Sibrand Poppema, Edmonton, both of Canada

[73] Assignee: Reasearch Corporation Technologies, Inc., Tucson, Ariz.

[21] Appl. No.: 09/018,282

[22] Filed: Feb. 4, 1998

Related U.S. Application Data

[63] Continuation of application No. 08/423,843, Apr. 18, 1995, abandoned, which is a continuation-in-part of application No. 08/071,009, Jun. 2, 1993, abandoned.

[51] Int. Cl.$^7$ .................. A61K 39/395; A61K 39/00; C07K 16/34; C07K 16/28; C07K 16/00
[52] U.S. Cl. .................. 424/130.1; 424/137.1; 424/141.1; 424/143.1; 424/144.1; 424/154.1; 424/156.1; 424/809; 424/810; 530/388.22; 530/388.75; 530/387.1; 530/387.5
[58] Field of Search .................. 530/388.22, 388.75, 530/387.1, 387.5; 424/130.1, 137.1, 141.1, 143.1, 144.1, 154.1, 156.1, 809, 810

[56] References Cited

U.S. PATENT DOCUMENTS

| | | | |
|---|---|---|---|
| 4,626,507 | 12/1986 | Trowbridge et al. | 435/240 |
| 5,100,899 | 3/1992 | Calne | 514/291 |
| 5,565,491 | 10/1996 | Schieven | 514/492 |

FOREIGN PATENT DOCUMENTS

| | | | |
|---|---|---|---|
| 0449769 | 10/1991 | European Pat. Off. | C07K 15/28 |
| 91/05568 | 5/1991 | WIPO | A61K 39/395 |
| 9105568 | 5/1991 | WIPO . | |
| 93/00431 | 1/1993 | WIPO | C12N 15/12 |
| WO95/14230 | 5/1995 | WIPO . | |
| WO96/32965 | 10/1996 | WIPO . | |

OTHER PUBLICATIONS

Lazarovits et al Transplantation vol. 54, No. 4, pp. 724–729 (1992) (also listed in the IDS).
Harlow et al (1988) Antibodies: A Laboratory Manual p. 287.
"Ortho MultiCenter Transplant Study Group. A Randomized Trial of OKT3 Monoclonal Antibody for Acute Rejection of Cadeveric Transplants", *N. Eng. J. Med.,* 313, 337–342, (Aug., 1985).
Benjamin, R.J., et al., "Induction of Tolerance by Monoclonal Antibody Therapy", *Nature,* 320, 449–451, (1986).
Bindon, C.I., et al., "Therapeutic Potential of Monoclonal Antibodies to the Leukocyte–Common Antigen", *Transplantation,* 40, 538–544, (1985).
Birkeland, M.L., et al., "Epitopes on CD45R (T200) Molecules Define Differentation Antigens on Murine B and T Lymphocytes", *J. Mol. Cell. Immunol.,* 4, 71–85, (Nov., 1988).

Brewer, Y., et al., "Effect of Graft Perfusion with Two CD45 Monoclonal Antibodies on Incidence of Kidney Allograft Rejection", *Lancet,* 935–937, (Oct., 1989).
Chatenoud, L. et al., "Anti–CD3 Antibody Induces Long–Term Remission of Overt Autoimmunity in Nonobese Diabetic Mice", *Proc. Natl Acad. Sci. USA,* 91, 123–127, (Jan., 1994).
Cosimi, A.B., et al., "In Vivo Effects of Monoclonal Antibody to ICAM–1 (CD54) in Nonhuman Primates with Renal Allografts", *J. Immunol.,* 144, 4604–4612, (1990).
Fabre, J.W., et al., "Immunosuppressive Properties of Rabbit Antibodies Against a Major Glycoprotein Restricted to Rat Leukocyte Membranes", *Transplantation,* 30, 167–173, (Sep., 1980).
Fabre, J.W., et al., "Quantitative Serological Analysis ofa Rabbit Anti–Rat Lymphocyte Serum and Preliminary Bio-Chemical Characterization of the Major Antigen Recognized", *Transplantation,* 23, 349–359, (Apr., 1977).
Fahey, J.L., et al., "Status of Immune–Based Therapies in HIV Infection and Aids", *Clin. Exp. Immunol.,* 88, 1–5, (Jan., 1992).
Hale, G., et al., "Pilot Study of Campath–1, a Rat Monoclonal Antibody that Fixes Human Complement, as an Immunosuppressant in Organ Transplantation", *Transplantation,* 42, 308–311, (Sep., 1986).
Harris, W.J., et al., "Therapeutic Antibodies—The Coming of Age", *Tibtech, vol. II,* Meeting Report, 42–44, (Feb., 1993).
Hasan, R., et al., "Evidence That Long–Term Survival of Concordant Xenografts is Achieved by Inhibition of Anti-species Antibody Production", *Transplantation,* 54, 408–413, (Sep., 1992).
Haug, C.E., et al., "A Phase I Trial of Immunosuppression With Anti–ICAM–1 (CD54) mAb in Renal Allograft Recipients", *Transplantation,* 55, 766–773, (Apr., 1993).
Imhof, B., et al., "Lymphatic Tissues In Vivo Immune responses", *Dekker.,* New York, (1991).
Isobe, M., et al., "Specific Acceptance of Cardiac Allograft After treatment with Antibodies to ICAM–1 and LFA–1", *Science,* 255, 1125–1127, (Feb., 1992).
Joliffe, L.K., "Humanized Antibodies: Enhancing Therapeutic Utility Through Antibody Engineering", *Intern. Rev. Immunol.,* 10, 241–250, (1993).
Jonker, M., et al., "The Influence of OKT8F Treatment on Allograft Survival in Rhesus Monkeys", *Transplantation,* 41, 431–435, (Apr., 1986).
Kirkman, R.L., et al., "A Randomized Prospective Trial of Anti–TAC Monoclonal Antibody in Human Renal Transplantation", *Transplantation,* 51, 107–113, (Jan., 1991).

(List continued on next page.)

*Primary Examiner*—Sheela Huff
*Assistant Examiner*—Geetha P. Bansal
*Attorney, Agent, or Firm*—Schwegman, Lundberg, Woessner and Kluth

[57] ABSTRACT

Compositions comprising anti-CD45RB antibodies are provided for the prevention or reversal of transplant rejection as well as therapy for autoimmune diseases.

16 Claims, 5 Drawing Sheets

OTHER PUBLICATIONS

Kirkman, R.L., et al., "The Effect of Anti–Interleukin–2–Receptor Monoclonal Antibody on Allograft Rejection", *Transplantation*, 40, 719–722, (Dec., 1985).

Knapp, W., et al., "Leucocyte Typing IV. White Cell Differentiation Antigens", *Oxford University Press*, 1070–1073, (1989).

Lai, R., et al., "Tissue Distribution of Restricted Leukocyte Common Antigens–A Comprehensive Study with Protein– and Carbohydrate–Specific CD45R Antibodies", *Laboratoy Investigation*, 64, See Table 2, 844–854, (Jun., 1991).

Lazarovits, A.I., *Tissue Antigens*, 33, 275, (1989).

Lazarovits, A.I., "T Lymophocyte Activiation and CD45/45R Antibodies (Mab)", *Tissue Antigen—Histocompatibility and Immunogenetics*,33, Abstract, 275, (Feb., 1989).

Lazarovits, A.I., et al., "A Monoclonal Antibody, 7G5 (CD7), Induces Modulation of Tp40 and Inhibits Proliferation in the Allogeneic and Autologous Mixed Lymphocyte Reactions", *Transplant. Proc.*, 20, 1253–1257, (Dec., 1988).

Lazarovits, A.I., et al., "Human Mouse Chimeric CD7 Monoclonal Antibody (SDZCHH380) for the Prophylaxis of Kidney Transplant Rejection", *J. Immunol.*, 150, 5163–5174, (Jun., 1993).

Lazarovits, A.I., et al., "Inhibition of Alloreactivity in Vitro by Monoclonal Antibodies Directed Against Restricted Isoforms of the Leukocyte–Common Antigen (CD45)", *Transplantation.*, vol. 54, No. 4, 724–729, (Oct., 1992).

Lazarovits, A.I., et al., "Prevention and Reversal of Renal Allograft Rejection by Antibody Against CD45RB", *Nature*, vol. 380, pp.717–720, (Apr., 1996).

Leonard, W.J., et al., "A Monoclonal Antibody that Appears to Recognize the Receptor for Human T–Cell Growth Factor; Partial Characterization of the Receptor", *Nature*, 300, 267–269, (1982).

Mathieson, P.W., et al., "Monoclonal–Antibody Therapy in Systemic Vasculitis", *N. Eng. J. Med.*, 323, 250–254, (Jul., 1990).

Nakakura, E.K., et al., "Potent And Effective Prolongation By Anti–LFA–1 Monoclonal Antibody Montherapy of Non–Primarily Vascularized Heart Alllograft Survival in Mice Without T Cell Depletion", *Transplantation*, 55, 412–417, (Feb., 1993).

Nicolls, M.R., et al., "Induction of Long–Term Specific Tolerance to Allografts in Rats by Therapy With an Anti–CD3–Like Monoclonal Antibody", *Transplantation*, 55, 459–468, (1993).

Nishikawa, M., et al., "Effects of Monoclonal Antibody against CD45RB on Peripheral Blood Mononuclear Cell Proliferation and on HLA–DR and Adhesion Molecule Expression on Thyrocytes of Patients with Autoimmune Thyroid Disease", *Thyroid*, vol. 5, No. 4, pp. 265–272, (1995).

Ogasa, N., et al., "Altered Expression of Cytokine Genes by CD45RB Monoclonal Antibody in Renal Allograft Rejection", *Transplantation Proceedings*, 27, No. 1, 398, (Feb., 1995).

Osaga, N., et al., "Altered Expression of Cytokine Genes by CD45RB Monoclonal Antibody in Renal Allograft Rejection", *Transplantation Proceedings*, 398, (Feb., 1995).

Ozcay, N., et al., "Prevention of heart allograft rejection by monoclonal antibody to CD45RB", *Turk. J. Surg.*, vol. 11, No. 6, pp. 372–376, (1995).

Pearson, T.C., et al., "Lymphocyte Changes Associated with Prolongation of Cardiac Allograft Survival in Adult Mice Using Anti–CD4 Monoclonal Antibody", *Clin. Exp. Immunol.*, 92, 211–217, (1993).

Pearson, T.C., et al., "The Assessment of Transplantation Tolerance Induced by Anti–CD4 Monoclonal Antibody in the Murine Model", *Transplantation*, 55, 361–367, (Feb., 1993).

Perico, N., et al., "Toward Novel Antirejection Strategies: In Vivo Immunosuppressive Properties of CTLA4Ig", *Kidney International*, 47, 241–246, (1995).

Poppema, S. et al., "Autobody MT3 is Reactive with a Novel Exon B–Associated 190–Da Sialic Acid–Dependent Epitope of the Leukocyte Common Antigen Complex", *The Journal of Immunology*, 147, No. 1, 218–223, (Jul., 1991).

Powelson, J.A., et al., "CDR–Grafted OKT4A Monoclonal Antibody in Cynomolgus Renal Allograft Recipients", *Transplantation*, 57, 788–793, (Mar., 1994).

Roitt, I.M., "Anti–Lymphocyte Serum", *Encyclopedia of Immunology*, Academic Press, London, 142–144, (1992).

Sandberg, G., "Anti–Lymphocyte Serum", *Encyclopedia of Immunology*, Academic Press, London, Roitt, I.M., ed., 142–144, (Dec. 1992).

Seaver, S.S., "Monoclonal Antibodies in Industry: More Difficult than Originally Thought", *Genetic Eng. News*, 14, 10–11, (1994).

Sempe, P., et al., "In Vivo Treatment With Monoclonal Antibodies", Imhof, B., 'Lymphatic Tissues in Vivo Immune Responses', Dekker, New York, 649–653, (1991).

Sempe, P., et al., "Role of CD4+CD45RA+T Cells in the Development of Autoimmune Diabetes in the Non–Obese Diabetic (NOD) Mouse", *Intern Immunol.*, 5, 479–489, (1993).

Shen, F.W., "Monoclonal Antibodies To Mouse Lymphocyte Differentiation Alloantigens", 25–31, (1981).

Stamenkovic, I., et al., "The B Lymphocyte Adhesion Molecule CD22 Interacts with Leukocyte Common Antigen CD45RO on T Cells and alpha2–6 Sialyltransferase, CD75, on B Cells", *Cell*, 66, 1133–1144, (Sep., 1991).

Streuli, M., et al., "Characterization of CD45 and CD45R Monoclonal Antibodies Using Transfected Mouse Cell Lines That express Individual Human Leukocyte Common Antigens", *J. Immunology.*, vol. 141, No. 11, 3910–3914, (Dec., 1988).

Waldmann, T.A., "Monoclonal Antibodies in Diagnosis and Therapy", *Science*, 252, 1657–1662, (Jun., 1991).

Yakura, H., et al., *Euro. J. Immunol.*, 19, 1505–1508, (1989).

Yakura, H., et al., "Alleviation of Autoimmunity in BXSB Mice by Monoclonal Alloantibody to Ly–5(CD45)", *Eur. J. Immunol.*, 19, 15505–1508, (1989).

Yakura, H., et al., "On The Function of Ly–5 In The Regulation of Antigen–Driven B Cell Differentiation", *J. Exp. Med.*, 157, 1077–1088, (1983).

Zhang, Z., et al., "Prevention and Reversal of Renal Allograft Rejection by Monoclonal Antibody to CD45RB in the Mouse Model", *Transplantation Proceedings*, vol. 27, No. 1, p. 389, (Feb. 1995).

Zhang, Z., et al., "Prevention and Reversal of Renal Allograft Rejection by Monoclonal Antibody to CD45RB in the Mouse Model", *Transplantation Proceedings*, 27, 389, (Feb., 1995).

PHARMACEUTICAL COMPOSITIONS COMPRISING ANTI-CD45RB ANTIBODIES FOR THE INHIBITION OF T-CELL MEDIATED IMMUNE RESPONSES

RELATED APPLICATION

This application is a continuation of Ser. No. 08/423,843, filed on Apr. 18, 1995 (ABN) which is herein incorporated by reference, which is a continuation-in-part application of U.S. Ser. No. 08/071,009 filed Jun. 2, 1993 (ABN) which is herein incorporated by reference.

FIELD OF THE INVENTION

This application relates to novel compounds and novel pharmaceutical compositions which are useful in modulating the immune response. The compounds comprise antagonists and agonists, especially to CD45RB antigens.

BACKGROUND OF THE INVENTION

Organ transplant rejection and the various autoimmune diseases are thought to be primarily the result of a T-cell mediated immune response. This T-cell mediated immune response is initially triggered by helper T-cells which are capable of so recognizing specific antigens. These helper T-cells may be memory cells left over from a previous immune response or naive cells which are released by the thymus and may have any of an extremely wide variety of antigen receptors. When one of these helper T-cells recognizes an antigen present on the surface of an antigen presenting cell (APC) or a macrophage in the form of an antigen-MHC complex, the helper T-cell is stimulated by signals emanating from the antigen-specific T-cell receptor, co-receptors, and IL-1 secreted by the APC or macrophage, to produce IL-2. The helper T-cells then proliferate. Proliferation results in a large population of T-cells which are clonally selected to recognize a particular antigen. T-cell activation may also stimulate B-cell activation and nonspecific macrophage responses. Some of these proliferating cells differentiate into cytotoxic T-cells which destroy cells having the selected antigen. After the antigen is no longer present, the mature clonally selected cells will remain as memory helper and memory cytotoxic T-cells, which will circulate in the body and recognize the antigen should it show up again. If the antigen triggering this response is not a foreign antigen, but a self antigen, the result is autoimmune disease; if the antigen is an antigen from a transplanted organ, the result is graft rejection. Consequently, it is desirable to be able to regulate this T-cell mediated immune response.

CD45 antigen (CD45) is expressed on most leukocytes. Indeed, it was previously thought that a common CD45 antigen was present on all leukocytes, for which reason the receptor was originally known as the Leukocyte Common Antigen (LCA). Monoclonal antibodies to CD45 were proposed as a means of effectively eliminating all leukocytes where desirable, for example, purging an organ to be transplanted of passenger leukocytes prior to transplantation using nonspecific CD45 monoclonal antibody. See, e.g., WO 91/05568.

CD45 is a protein tyrosine phosphatase, and it participates in T-cell activation by dephosphorylating the protein tyrosine kinase P56lck at a tyrosine residue.

It has recently been shown that different isoforms of CD45 are generated by alternate splicing of a single primary transcript of the CD45 gene. These CD45 isoforms include CD45RA, CD45RB, and CD45RO. CD45RA contains the expression products of exons 4, 5, and 6 (sometimes referred to as A, B, and C) of the CD45 gene; CD45RB contains the expression products of exons 4 and S, but not 6; CD45RO does not contain the expression products of any of the three exons 4, 5, or 6. See Hall et al, "Complete Exon-Intron Organization of the Human Leukocyte Common Antigen (CD45) Gene", J. IMMUNOLOGY, Vol. 141, pp. 2781–2787 (1988), herein incorporated by reference and Sheu et al, "Characterization of CD451 and CD45R Monoclonal Antibodies using Transfected Mouse Cell Lines that Express Individual Human Leukocyte Common Antigens", J. IMMUN., Vol. 141, pp. 3910–3914, No. 11 (1988), herein incorporated by reference. The significance of this variable expression, however, has been unclear.

It has now been discovered that different types of T-cells may predominantly express one or another of these CD45 isoforms of CD45 expression. Naive helper T-cells and memory T-cells express predominately CD45RA and CD45RO respectively. CD45RB expression is more variable, but it appears to be expressed on naive helper T-cells and especially on naive cells which have been stimulated to proliferate. CD45RB expression is down-regulated as the cells become activated. It has now been shown that compounds which suppress CD45RB expression but not CD45RO expression are capable of selectively inhibiting the T-cell mediated immune response without destroying the pool of memory T-cells. CD45RB is of particular interest because if CD45RB function is suppressed, the proliferating cells will fail to mature, and as a result the antigen specific clone they comprise will be deleted. Consequently, CD45RB suppressors have a great advantage over current immunosuppressants in that (i) they act on a particular T-cell population rather than having an overall immunosuppressive effect, thereby avoiding the risk of side effects associated with over-suppression of the immune system; and (ii) they are capable of conferring long term tolerance to a particular antigen when they are administered contemporaneously with exposure to antigen, e.g., just before and after an organ transplant or during an acute phase of an autoimmune disease.

SUMMARY OF THE INVENTION

In a first embodiment, therefore, the present invention relates to CD45 suppressors and pharmaceutical compositions containing the same which modulate the immune response by binding specifically to CD45RB, especially monoclonal antibodies to CD45RB and fragments of the monoclonal antibodies having such properties.

S. Poppema, et al., J. IMMUNOLOGY (July 1991) 147: 218, incorporated herein by reference, have previously described the monoclonal antibody MT3. This publication, however, does not disclose a detailed method for making this antibody, nor does it disclose any pharmaceutical use for this antibody and, therefore, necessarily fails to disclose the T-cell population recognized by this antibody. A. Lazarovits, et al., Transplantation (October 1992) 54: 724, incorporated herein by reference, has characterized the in vitro effect of this antibody. Lazarovits, for the first time, showed that MT3 mAb inhibits proliferation of and generation of T-cells by interfering with CD45RB (a leukocyte surface molecule) and Lazarovits indicated that such interference may be the basis for in vivo therapy. Since the publication of this paper experiments described herein have confirmed such optimism. In addition to MT3 mAb, Lazarovits reports that monoclonal antibodies to CD45RB, such as antibodies produced from the cell line HB220 which is publicly available from the ATCC, 10801 University Blvd., Manassas, Va. 20110-2209, bind to CD45RB and are effective agents in inhibiting immune function in vitro and in vivo function (see U.S. Ser. No. 08/071,009 filed Jun. 2, 1993 herein incorporated by reference).

Poppema and Lazarovits have now found that 6G3 monoclonal antibody binds to CD45RB. This is a murine IgGi directed against human CD45RB. It cross reacts with monkey CD45RB. Lazarovits has also now found that monoclonal antibodies from the cell line HB220 (designated CD45RB mAb (MB23G2), the 6G3 monoclonal antibody and the MT3 mAb bind to neuraminidase sensitive epitopes on leukocytes including T-cells and inhibit the tyrosine phosphorylation of phospholipase C-γ1. It is of interest to note that HB223 (now designated MB4B4), an analogous anti-CD45RB antibody to those of the invention, is found not to bind to neuraminidase sensitive epitopes. It is also observed that B4B4 binds to a neuraminidase insensitive epitope and does not prevent the tyrosine phosphorylation of phospholipase C-γ1.

Given these antibodies it is of course possible to alter or produce recombinant antibodies which may then be cloned and expressed by conventional techniques, e.g., as described in EP 0 449 769 incorporated herein by reference. The term antibody, antibody fragments, fusion compounds, chimeric compounds and derivatives thereof are collectively termed compounds or suppressors throughout the specification.

In a second embodiment, the present invention provides suppressor compounds and pharmaceutical compositions capable of modulating the immune response by competing with CD45RB for its binding site in vivo.

In another embodiment, the present invention relates to methods of in vivo immunosuppression. The methods include pre-treatment in vivo therapies to prevent rejection of transplanted organs and post-transplant in vivo therapies to reverse an immune response.

The methods also include in vivo treatment of autoimmune diseases.

DETAILED DESCRIPTION OF THE INVENTION

Figure 1:
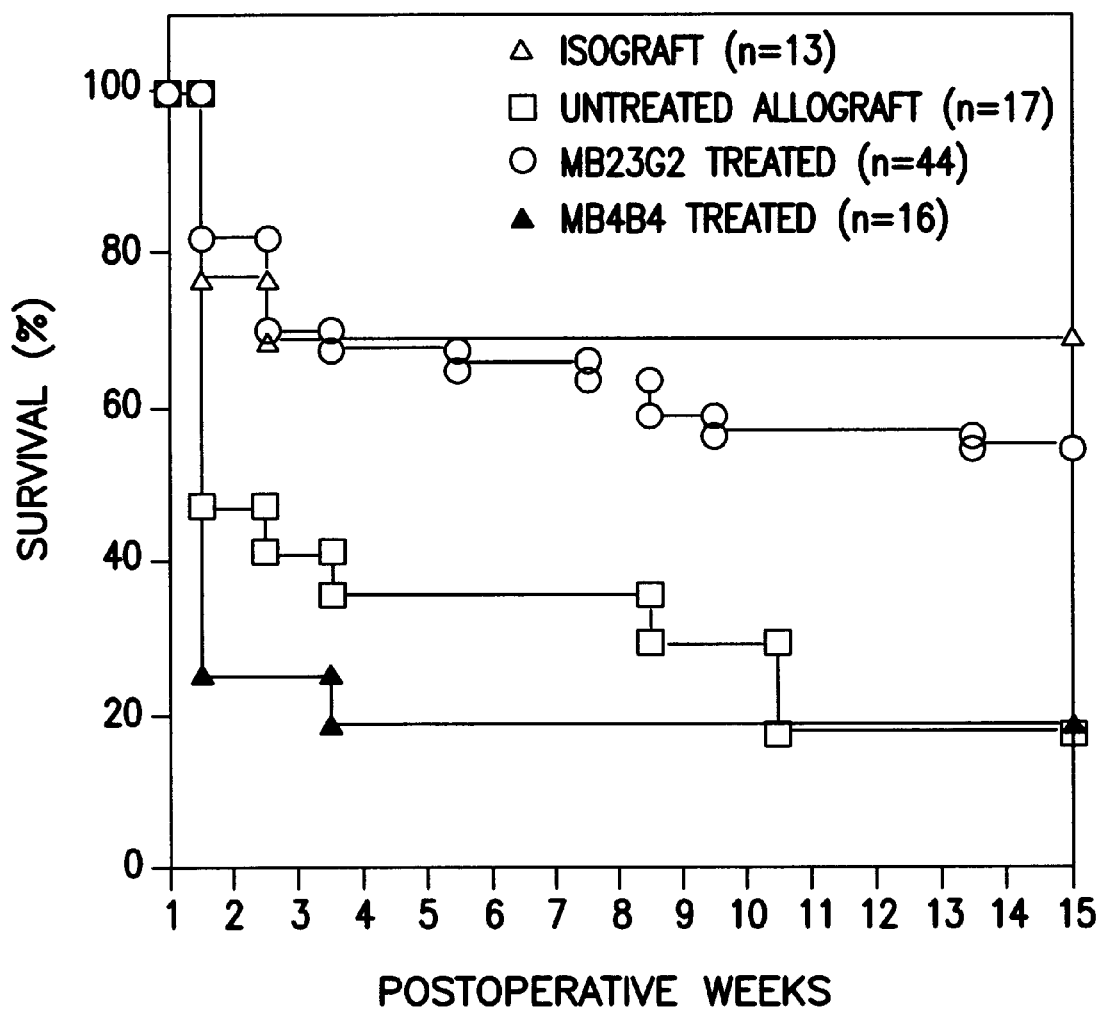
FIG. 1 shows prolonged survival of MB23G2-treated animals compared to an untreated group.

The suppressors of the invention are preferably produced as described in the following examples, or by equivalent means as would be apparent to one skilled in the art.

It will be understood by those skilled in the art that the hybridomas herein referred to may be subject to genetic mutation or other changes while still retaining the ability to produce monoclonal antibody of the same desired specificity. The present invention therefore encompasses mutants, other derivatives and descendants of the hybridomas.

It will be further understood by those skilled in the art that a monoclonal antibody can be subjected to the techniques of recombinant DNA technology to produce other derivative other antibodies or chimeric molecules which retain the specificity of the original monoclonal antibody. Such techniques may involve combining DNA encoding the immunoglobulin variable region, or the complementary determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, GB 2188638A, herein incorporated by reference).

EP-A-0 120 694 (Boss et al/Celltech, herein incorporated by. reference) describes the cloning and expression of chimeric antibodies. In these derivatives the variable domains from one immunoglobulin are fused to constant domains from another immunoglobulin. Usually, the variable domains are derived from an immunoglobulin gene from one species, for example a mouse or a rat, and the constant domains are derived from an immunoglobulin gene from a different species, perhaps a human. This technology is now very well known in the art. A later European Patent Application, EP-A-0 125 023 (Cabilly/Genetech, herein incorporated by reference), also U.S. Pat. No. 4,816,567, describes much the same subject as the Boss patent application, but describes production of other variations of immunoglobulin-type molecules using recombinant DNA technology.

Another possibility is to attach just the variable region of the monoclonal antibody to another non-immunoglobulin molecule, to produce a derivative chimeric molecule (see WO 86/01533, Neuberger and Rabbits/Celltech, herein incorporated by reference). A further possibility would be to produce a chimeric immunoglobulin having different specificities in its different variable regions, e.g., the monoclonal antibodies of the present invention (see EP 68763a). Yet another possibility would be to produce a mutation in the DNA encoding the monoclonal antibody, so as to alter certain of its characteristics without changing its essential specificity. This can be done by site-directed mutagenesis or other techniques known in the art.

The Winter patent application EP-A-0 239 400 (herein incorporated by reference) describes how it is possible to make an altered, derivative, antibody by replacing the complementarity determining regions (CDRs) of a variable region of an immunoglobulin with the CDRs from an immunoglobulin of different specificity, using recombinant DNA techniques—so called "CDR-grafting" This enables antigen-binding specificity of one antibody. (In the present case it might be MT3 or 6G3 or an antibody with the same binding specificity or an antibody which is cross-reactive with MT3 or 6G3 to be transferred to another antibody.) This enables "humanization" of antibodies. A "humanized" antibody with the CDRs of a rodent antibody specific for an antigen of interest, might well be less likely to be recognized as foreign by the immune system of a human. It follows that a "humanized" antibody with the same binding specificity as e.g., MT3 or 6G3 cross-reacts with either (see later), might well be of particular use in human therapy and/or diagnostic methods. The use of antibodies according to the present invention are discussed later in the text. All such uses of the monoclonal antibody are encompassed by the present invention.

As discussed, the state of the art is such that the person skilled in the art well knows how to manipulate and alter any given antibody or gene(s) encoding for the same to generate a derivative to suit his or her particular needs.

The provision of an antibody such as MT3 or 6G3 allows persons skilled in the art to obtain binding partners, e.g. antigens/epitopes or antibody/paratopes which bind to it. Therefore, the present invention also provides binding partners, e.g. antigens and/or antibodies which bind with an antibody or derivatives thereof as hereby provided, such as MT3 and 6G3.

The binding partners obtained by use of the MT3 mAb and 6G3 mAb may also be used to produce additional ligands e.g. antibodies (or molecules having antibody-like binding function e.g. fragments, derivatives and synthetic analogues of antibodies) other than the MT3 or 6G3 mAb. Therefore, also provided are ligands e.g. mAbs which are able to bind with a binding partner which is able to bind with the MT3 mAb and 6G3 mAb. Such ligands ("cross-reactive ligands") e.g. mAbs may recognize the same epitope as recognized by MT3 mAb and 6G3 mAb on said binding partner.

The present invention also provides derivatives, functional equivalents (e.g. a molecule having an antibody-like binding specificity) and fragments of said cross-reactive ligands, perhaps produced using one or more of the techniques of recombinant DNA technology referred to and discussed above. Also included are single domain ligands (mAbs) as described in WO 90/05144 (herein incorporated by reference).

Using standard techniques, it is possible to use a ligand, e.g. antibodies of the present invention and derivatives thereof, in immunopurification of a binding partner antigen. Techniques for immunoaffinity column purification are well known, see for instance "Current protocols in Immunology", ed. J. E. Coligan et al, John Wyley and Sons, Unit 8.2 (herein incorporated by reference). In fact, it should be possible to use an immunoaffinity column to isolate cross-reactive ligands as discussed above, without needing to isolate the antigens themselves. A first round of immunoaffinity purification uses a ligand, e.g. MT3, 6G3, etc. mAb to remove from a sample the antigen-containing binding partner, which may then be used in the column to select, from a heterogeneous population of ligands, those ligands which are cross-reactive with the MT3 mAb, 6G3 mAb, etc. and recognize the same binding partners.

A binding partner isolated using the ligand, e.g. the MT3, 6G3, etc. mAb may be used to select cross-reactive ligands from a repertoire or heterogenous population of antibodies generated by a whole variety of means. One way is to select monoclonal antibodies and cell lines producing them by the standard hybridoma techniques. Also provided by the present invention are immortalized cells e.g. hybridomas producing said cross-reactive ligands.

Another way of selecting ligands which are cross-reactive with a ligand such as the MT3 mAb or 6G3 mAb is to use the methods for producing members of specific binding pairs disclosed in WO 92/01047 (Cambridge Antibody Technology Limited and MRC/McCafferty et al, herein incorporated by reference). This discloses expression of polypeptide chain components of a genetically diverse population of specific binding pair members, such as antibodies, fused to a component of a secreted replicable genetic display package (RGDP), such as a bacteriophage, which thereby displays the polypeptide on the surface. Very large repertoires of displayed antibodies may be generated, and screened by means of antigen binding to obtain one or more antibodies of interest, along with their encoding DNA. DNA encoding for a polypeptide displayed on the surface of an RGDP is contained within the RDGP and may therefore be easily isolated and cloned for expression. The antibody repertoire screen may of course be derived from a human source. obviously, once one has an immortalized cell line, e.g. a hybridoma, or an RGDP containing DNA encoding at least a polypeptide component of a binding ligand, one skilled in the art is in a position to obtain (according to techniques well known in the art) the entire nucleotide sequence encoding the ligand, e.g. the mAb secreted by the cell. Therefore, the present invention also encompasses primary nucleotide sequences which encode the ligands, e.g. mAbs as defined above, together with fragments of these primary sequences and secondary nucleotide sequences comprising derivatives, mutations and hybridizing partners of said primary nucleotide sequences.

These nucleotide sequences may be used in a recombinant system to produce an expression product according to standard techniques. Therefore, the present invention includes vectors (cloning and expression vectors) incorporating said nucleotide sequences, transformed cells incorporating said vectors and expression products produced by use of a recombinant system utilizing any such vectors or transformed cells.

The production of fusion proteins is also contemplated. See for instance Stamenkovic et al, "The B Lymphocyte Adhesion Molecule CD22 Interacts with Leukocyte Common Antigen CD45RO on T Cells and α2-6 Sialytransferase, CD75, on B Cells", CELL, Vol. 66, pp. 11–33–1144 (1991), herein incorporated by reference.

The present invention also includes methods for expressing a ligand, e.g. a mAb, derivative, functional equivalent or fragment thereof, which comprises using a nucleotide sequence, vector or transformed cell as defined above.

More specifically, MT3 and 6G3 which are mAbs directed against the CD45RB antigen will bind to an epitope on CD45RB in human cells expressing CD45RB. This epitope may then be purified, for instance utilizing an immunoaffinity column (as discussed), and partially or wholly sequenced, for instance using repeated rounds of Edman degradation.

EXAMPLE 1

Murine Monoclonal Antibody to CD45RB

Murine monoclonal antibody to human CD45RB is produced by using conventional techniques, essentially as described by Kohler and Milstein in Nature 256: 49. Female BALB/C mice (20–25 g) each receive 100 µg of antigen containing human CD45RB, e.g., Hodgkin cell line DEV (publicly available), by i.p. injection. (Alternatively, the antigen may comprise murine cells which have been transformed to express human CD45RB). After 2 weeks a second booster injection comprising 50 µg of the antigen is administered, again by i.p. injection. The presence of antibodies reactive to the antigen in the animals' blood serum is confirmed by immunohistologic screening. Mice displaying maximum blood serum levels of CD45RB antibody receive another booster injection comprising 20 µg of antigen. Four days later, they are sacrificed and their spleen cells are isolated and fused with a suitable myeloma line, e.g., myeloma X63 (publicly available). The resulting hybridoma are cultured and selected for expression of antibody having a high affinity to CD45RB.

A hybridoma line producing murine monoclonal antibody to human CD45RB is the MT3 hybridoma line, which was deposited on Mar. 29, 1993 under the Budapest Treaty with the American Type Culture Collection (ATCC), 10801 University Blvd., Manassas, Va. 20110-2209/U.S.A. under ATCC accession no. HB11312.

A second hybridoma cell line, which produces rat monoclonal antibody to murine CD45RB is HB220 (now designated MB23G2), which has been deposited with the ATCC and is available by purchase from the ATCC under the Budapest Treaty on Apr. 11, 1995.

A third hybridoma cell line (deposited with the ATCC as HB-11873), produces antibodies of the invention (6G3 mAb). This hybridoma cell line was produced by the fusion of myeloma cell line SP2/O and spleen cells from a mouse immunized with human large cell B cell non-Hodgkin lymphoma cell line VER. The resulting clones were screened by an immunoperoxidase procedure on frozen tissue sections of human tonsil and rhesus monkey spleen. Clone 6G3 was selected for its high reactivity with subsets of T and B lymphocytes in both tissues. The antibody reactivity was characterized as CD45RB by its selective reactivity with human CD45RB expressing transfectants and by the characterization of the molecular weight of the antigen as three bands with of 220, 204 and 190 kD. The reactivity of the antibody could be abolished by pretreatment of tissues, cells or blots with neuraminidase, indicating the sialic acid dependence of the antigen.

A fourth hybridoma cell line, HB223 produces analogous monoclonal antibodies to MB23G2; it is also deposited and available through the ATCC.

EXAMPLE 2

Chimeric Monoclonal Antibody to CD45RB a) Cloning of the gene encoding the variable domain of the heavy chain The genomic DNA of the desired hybridoma, in this example the MT3 or 6G3 hybridomas of Example 1, and of the parental myeloma cell lines of the hybridomas (myeloma X63 or SP2/O) is isolated and digested with EcoRI. Each digested DNA is then fractionated on the same agarose gel. After migration, the agarose gel is analyzed by Southern blot using as probe a 32p labelled 0.7 kb XbaI-EcoRI DNA fragment which encodes the murine heavy chain enhancer E$\mu$ (Heinrich et al, J. OF IMMUNOL. (1989) 143: 3589) to identify the desired variable heavy chain fragment, i.e., the desired fragment is present in the MT3 AND 6G3 hybridomas but not in the X63 or SP2/O myelomas. Further purification of this fragment is then carried out by preparative agarose gel electrophoresis.

DNA fragments of the same size as the desired fragment are cloned in the EcoRI restriction site of bacteriophage ZAP (Stratagene). Using the probe described above, the recombinant phages are screened and clones selected which hybridize to the probe. The DNA inserts of the selected clones are amplified on phage plate lysate by polymerase chain reaction (PCR) using as primers, a first oligonucleotide encoding the murine $J_z$ gene and a second oligonucleotide encoding the beginning of the MT3 or the 6G3 heavy chain. The DNA fragments obtained from each of the selected clones are analyzed by Southern blot using as probe an oligonucleotide encoding a portion of the E$\mu$ probe described above.

b) Construction of a chimeric heavy chain gene

The EcoRI fragment (comprising the gene of the MT3 or 6G3 heavy chain variable domain (including the promoter and the enhancer)) is obtained by digestion of the DNA of one of the phage clones selected in step a)is then cloned into the EcoRI restriction site of the eukaryotic expression vector pSV2 neo-human $\gamma_1$, constant part (Heinrich et al, supra). Following propagation of the resulting plasmid, the nucleotide sequence of the gene encoding the MT3 OR 6G3 heavy chain variable domain is redetermined to exclude the possibility that a mutation in this gene has occurred.

c) Cloning of the gene encoding the variable domain of the light chain

The genomic DNA of the MT3 or 6G3 hybridomas and of the parental cell lines X63 or SP2/O is isolated and digested with EcoRI. Each digested DNA is then fractionated on the same agarose gel. After migration, the agarose gel is analyzed by Southern blot using as probe a $^{32}$P-labelled DNA fragment comprising the five mouse $J_\kappa$ genes and the mouse $C_\kappa$ gene. Size fractionated EcoRI fragments corresponding in size to the desired MT3 or 6G3 light chain variable domain are cloned in phage EMBL4 (Stratagene).

A clone containing the DNA fragment encoding the MT3 or 6G3 light chain is identified by screening the recombinant phage clones with the probe described immediately above. The desired DNA fragment is then subcloned into the EcoRI-XbaI site of pGEM4 (Promega) and its sequence determined.

d) Construction of a chimeric light chain gene

An XbaI—XbaI fragment containing the sequence encoding the murine heavy chain enhancer (Heinrich et al; supra) and a HindIII-SphI DNA fragment containing the sequence for the human κ constant part (huCκ) are cloned together into phage mp18 (Stratagene). Site-directed mutagenesis is performed on the resulting recombinant phage to disrupt the HindIII site in the desired coding region and followed by digestion with EcoRI and HindIII to generate a DNA fragment containing the sequences for both (E$\mu$) and (huCκ). After filling in the ends of this fragment, the fragment is subcloned into the blunt-ended EcoRI-BamHI site of pSV2-DHFR to generate pSV2-DHFR-E$\mu$-huC$_\kappa$. pSV2-DHFR is obtained by replacing the BamHI - HindIII fragment of pSV2-neo with a BamHI-HindIII fragment encoding the dihydrofolate reductase gene.

Lastly, an EcoRI-XbaI DNA fragment containing the MT3 or 6G3 light chain sequence is isolated from the recombinant pGEM4 plasmid of step 3 and subcloned into pSV2-DHFR-E$\mu$-huC$_\kappa$ to generate pSV2-DHFR-E$\mu$-huC$_\kappa$-MT3$_L$ or pSV2-DHFR-E$\mu$-huC$_\kappa$-6G3$_L$.

e) Expression of chimeric antibody

The plasmids as obtained in steps b) and d) are co-transferred into the mouse myeloma cell line SP2/0 (ATCC CRL 1581) by electroporation using a gene pulser apparatus from Biorad. This technique is known to create stable transfectants at a high frequency. The SP2/0 cell line fails to produce endogenous heavy and light chains and is sensitive to Geneticin (G 418) at a concentration of 0.8 mg/l.

SP2/0 cells are grown in the usual growth medium (RPMI+10% FCS 5×10$^{-5}$ β-mercaptoethanol) harvested in the log phase of growth and washed with the electroporation buffer (Bio-Rad). Cell concentration is adjusted to 2×10$^7$ cells/ml. To 0.8 ml of the cell suspension is added 15–20 $\mu$g of each plasmid. The mixture is placed on ice and left to stand for 10 min. Then the cells are subjected to an electrical pulse (280 Volt; 25° F.) and again left to stand for 15 min. Cells are transferred to the usual growth medium and incubated at 37° C. in a CO$_2$ incubator.

After a 3-day incubation, selection of G 418 resistance is started. Cells are re-suspended in fresh medium containing 1.4 mg/ml G 418. The cultures yield growing cells after 10–14 day-incubation in the presence of G 418. After the 2-week incubation, supernatants of the confluent cultures are tested for human IgG expression in a sandwich-type ELISA (anti-human κ-light chain/supernatant/anti-human IgG-alkaline phosphatase conjugate).

This test indicates that complete antibody molecules are secreted in all cultures at varying concentrations in the range of 50–500 ng/ml.

To select cells in which the DHFR gene is amplified and therefore secrete high amounts of the desired antibody, two selection procedures for Methotrexate (MTX) resistance are carried out as described below. For this purpose, the G 418 resistant cell pools are each divided and amplification is preformed either according to procedure A (MTX increase by a factor of 2 or 2.5) or procedure B (MTX increase by a factor of 5).

| Procedure A | Procedure B |
| --- | --- |
| 100 nM MTX | 200 nM MTX |
| 250 nM MTX | 1 μM MTX |
| 500 nM MTX | 5 μM MTX |
| 1 μM MTX | 25 μM MTX |
| 2.5 μM MTX | 100 μM MTX |
| 5 μM MTX | |
| 10 μM MTX | |
| 25 μM MTX | |
| 100 μM MTX | |

Each amplification step comprises inoculating the cells at a density of $2 \times 10^5$ cells/ml in the usual growth medium supplemented with G 418 at 1.4 mg/ml and with MTX at the concentration of choice. After 72 hour incubation, cells and the supernatant are separated. Antibody secretion is monitored either by ELISA or by HPLC using a protein A column. Most of the pools reach a maximum of specific antibody production at a certain MTX concentration. The best producing pools are cloned by limiting dilution. Out of several hundred analyzed clones, 15 best producing clones are selected. Productivity of the clones ranges from 30 to 50 mg mAb/$10^9$ cells in 72 hours.

The antibody is purified from a culture supernatant by elution on a protein A affinity column.

The compounds and pharmaceutical compositions of the invention (the Compounds) are useful in immunomodulation, especially immunosuppression, e.g., in the following indications:

a) Treatment and prevention of organ or tissue transplant rejection, e.g. for the treatment of recipients of e.g. heart, lung, combined heart-lung, liver, kidney, pancreatic, skin, small bowel, or corneal transplants. They are also indicated for the prevention of graft-versus-host disease, such as sometimes occurs following bone marrow transplantation.

b) Treatment and prevention of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases for which the compounds of the invention may be employed include, autoimmune hematological disorders (including, e.g. hemolytic anemia, aplastic anemia, pure red cell anemia and idiopathic thrombocytopenia), systemic lupus erythematosus, polychondritis, scleredema, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary biliary cirrhosis, juvenile diabetes (diabetes mellitus type 1), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) Treatment of leukemias characterized by over-proliferation of T-lymphocytes, including virally induced leukemias, e.g., HTLV-1-induced leukemia.

The compounds of the invention are shown to prevent mice from rejecting kidney transplants and induces long term survival. The compounds of the invention are also shown to reverse and prevent rejection of organ transplants in primates.

The Compounds may be used alone, or in conjunction with conventional immunosuppressant and anti-inflammatory drugs, e.g., Cyclosporin, FK-506, Rapamycin, corticosteroids, mycophenolate mofetil, Leflunomide and others. The Compounds may also be used in combination with other monoclonal antibodies or other compounds specifically recognizing particular lymphocyte sub-populations, e.g., CD25 mAbs, CTLA4-Ig fusion peptide, etc.

The Compounds have a particular advantage over conventional immunosuppressants and anti-inflammatory drugs in that they are capable of inducing long term tolerance to an antigen when the subjects are treated with the Compounds simultaneously to exposure to the antigen. It is believed that T-cells having a receptor for the antigen are anergized, and that this T-cell clone is effectively deleted. That is, it is not enough that the T-cell recognize a foreign protein, it requires the presence of a second signal, i.e., that of CD45. If CD45 is not recognized the T-cell clone is deleted. For example, we have shown that in a mouse kidney transplant model, allograft tolerance following initial treatment with CD45RB monoclonal antibody persists indefinitely, with survival well in excess of 100 days.

EXAMPLE 3

In Vivo Prevention of the Rejection of Kidney Transplants

In this experiment a right nephrectomy was performed on 18 mice at the same time an allograft (kidney transplant from a different strain of mouse) was performed. A contralateral nephrectomy was followed on the seventh postoperative day (POD 7), so that from that point on, the animals relied only on the allografted kidney. Nine of the mice were treated with 50 μg mixtures of rat anti-mouse CD45RB monoclonal antibody produced from cell lines HB220 and HB223 by iv for the first two days (POD 0 and POD 1) followed by 100 μg of each antibody intraperitoneally for 9 days (POD 2 to POD 10). Of the nine control animals which did not receive the antibody, seven were dead three days after the second kidney was removed, and the remaining two exhibited severe rejection one week later. Of the nine animals treated with the antibody, there were three deaths due to surgical complications unrelated to any immune response, but remarkably, the remaining six animals survived long term (e.g., over 100 days) without any further treatment and without any evidence of allograft rejection. In a third group of 10 untreated isograft recipients, the incidence of death due to surgical complication was the same. There was no significant difference between the serum creatinine levels of the allograft group receiving monoclonal antibody and the isograft group, indicating that the kidneys in both groups were functioning normally.

EXAMPLE 4

In Vivo Prevention of the Rejection of Small Bowel Transplants

In this experiment the native small bowels of ten mice were left intact and at the same time an allograft was performed (heterotopic transplant). Six of the ten mice were treated with 50 µg mixtures of rat anti-mouse CD45RB monoclonal antibody produced from cell lines HB220 and HB223 by iv for the first two days (POD 0 and POD 1) followed by 100 µg of each antibody intraperitoneally for 9 days (POD 2 to POD 10). The 4 animals that did not receive antibody therapy were all dead on POD 7. Two of the six mice receiving the antibody therapy died by the seventh day. These deaths were technical losses due to surgical complications unrelated to any immune response; however, remarkably, the remaining four treated animals survived beyond 100 days. Table I below summarizes the results of this experiment:

TABLE I

PREVENTION OF REJECTION OF SMALL BOWEL TRANSPLANTS IN MICE

| MOUSE | THERAPY | SURVIVAL DAYS | CLINICAL REJECTION | CAUSE OF DEATH |
|---|---|---|---|---|
| 1 | NONE | 7 | +++ | REJECTION |
| 2 | NONE | 7 | +++ | REJECTION |
| 3 | NONE | 6 | +++ | REJECTION |
| 4 | NONE | 7 | +++ | REJECTION |
| 5 | CD45RB | 14 | +/− | SACRIFICE |
| 6 | CD45RB | >100 | +/− | — |
| 7 | CD45RB | >100 | +/− | — |
| 8 | CD45RB | >100 | +/− | — |
| 9 | CD45RB | 7 | − | TECHNICAL |
| 10 | CD45RB | 6 | − | TECHNICAL |

EXAMPLE 5

Reversal of the Rejection of Kidney Transplants in Mice

In this experiment a right nephrectomy was performed on 10 mice at the same time an allograft (kidney transplant from a different strain of mouse) was performed.

All ten of the animals were observed for five days without immunosuppression therapy. These animals were known to be experiencing severe rejection at this stage because sacrificed control animals, also subjected to a nephrectomy and an allograft kidney transplantation, exhibited severe rejection on day S.

On POD 5 four of the animals were given three daily intraperitoneally 25 µg doses of antiCD45RB antibody (from cell lines HB220 (CD45RB MB23G2 mAb) and HB223 (CD45RB MB4B4 mAb)) for the next three days. All four of the animals experienced rapid reversal of their rejection symptoms, including a return to normal levels of creatinine, and lived greater than 100 days. The untreated animals died by day nine due to organ rejection. Table II summarizes the results of this experiment:

TABLE II

REVERSAL OF THE REJECTION OF KIDNEY TRANSPLANTS IN MICE

| MOUSE | THERAPY | SURVIVAL DAYS | CAUSE OF DEATH |
|---|---|---|---|
| 1 | NONE | 8 | REJECTION/UREMIA |
| 2 | NONE | 9 | REJECTION/UREMIA |
| 3 | NONE | 8 | REJECTION/UREMIA |
| 4 | NONE | 9 | REJECTION/UREMIA |
| 5 | NONE | 9 | REJECTION/UREMIA |
| 6 | NONE | 9 | REJECTION/UREMIA |
| 7 | CD45RB | >100 | — |
| 8 | CD45RB | >100 | — |
| 9 | CD45RB | >100 | — |
| 10 | CD45RB | >100 | — |

This data with respect to reversal is significant in confirming that the antibody therapy is truly effective in suppressing an immune response. Treatment and cures are accomplished with antibody therapy.

EXAMPLE 6

Confirming Results Using MB23G2 and MB4B4 Separately

Recipient Bald/c (h-2d) mice had the right kidney removed before receiving a transplanted kidney from donor C57B1 (h-2b) mice. A left native nephrectomy was subsequently performed on day 7. There were four groups of animals. Thirteen received isografts, 17 received allografts with no immunosuppression (vehicle control), 44 received allografts and were given two doses of purified rat anti-mouse CD45RB mAb MB23G2 1 mg/kg (30 µg) intravenously on days 0 and 1, and 16 received allografts but were treated with two doses of purified rat anti-mouse CD45RB mAb MB4B4 1 mg/kg (30 µg) intravenously on days 0 and 1. No further immunosuppression was given.

Figure 2:
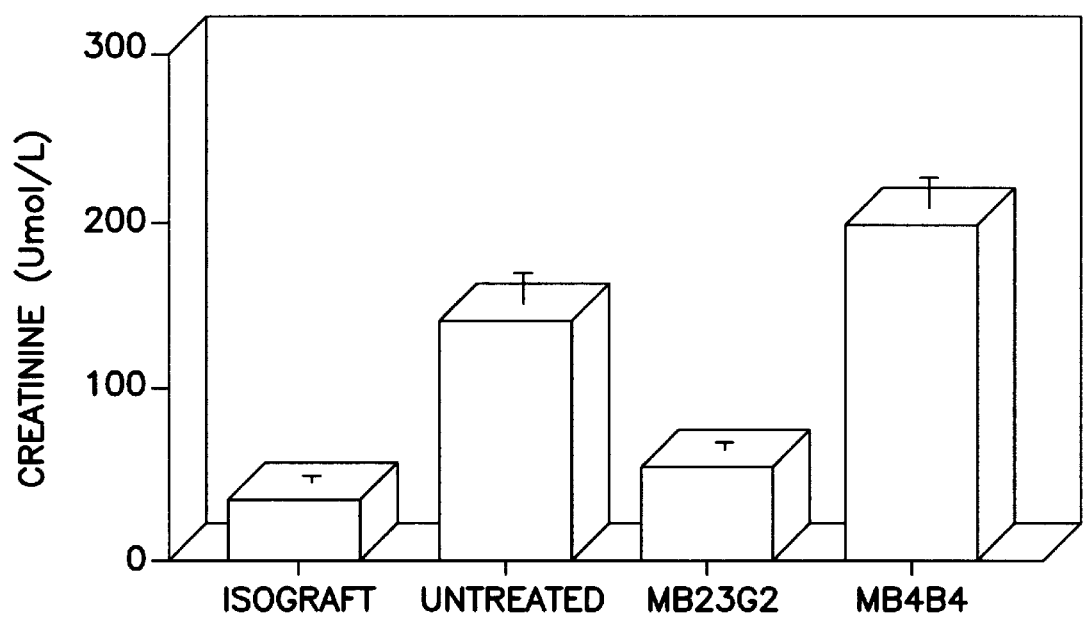
FIG. 2 shows the serum creatine levels from each group at the time of sacrifice.

As expected, the MB23G2 treated animals had prolonged survival compared to the untreated group (p<0.002) (see FIG. 1) and was comparable to the isograft group. Remarkably the CD45RB MB4B4 was no better than the vehicle alone at preventing rejection. Both MB23G2 and MB4B4 are IgG2a but a difference exists between them. Both mAbs bind to Balb/C leukocytes as assayed by FACS. FIG. 2 shows the serum creatinine in animals from each group at the time of sacrifice, or beyond day 100 for the long-term survivors. There were no differences between the isograft and MB23G2 treated groups, while the untreated and MB4B4 treated animals died from uremia.

Figure 3:
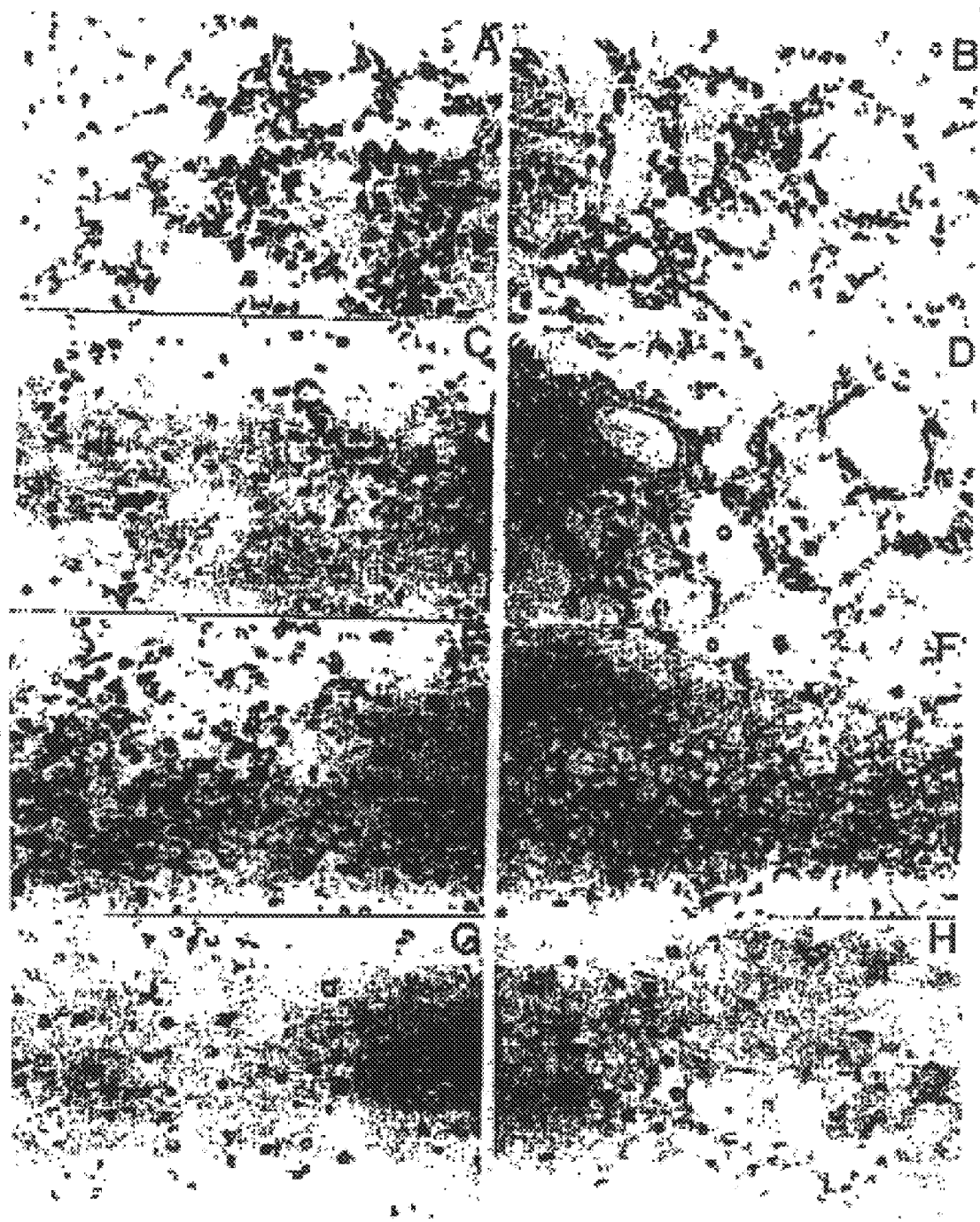
FIG. 3(A–H) demonstrates immuno peroxidase microscopic studies on untreated and treated allografts.

FIG. 3 demonstrates immunoperoxidase microscopic studies performed on an untreated and on a MB23G2 treated renal allograft both on day 7. A mononuclear cell infiltrate is seen, consisting mainly of CD3+ T cells (panels A and B). Interestingly, there were more cells of the CD4+ phenotype in the MB23G2 treated animals than in the untreated animals (panels C and D). In contrast there were more cells of the CD8+ phenotype in the untreated animals than in MB23G2 treated animals (panels E and F). Thus, the MB23G2 treated animals demonstrated an elevated CD4:CD8 ratio compared to untreated animals. Remarkably, few of the infiltrating cells were CD45RB positive, (panels G and H) a particularly notable finding considering that the CD45RB mAb MB23G2 could reverse acute rejection.

To assess the possibility of antigen specific tolerance (Table II) skin transplants were performed on 13 animals which had maintained a kidney transplant beyond 100 days after receiving 2 does of MB23G2 mAb at the time of renal allografting. Each animal received full thickness skin allografts from a C57B1/6 mouse (isogeneic with the donor of the renal allograft) and a control skin transplant: 9 received a Balb/C isograft and 4 received a CBA allograft (third party donor). No further immunosuppression was given. Of the 13 animals with kidney specific tolerance, there was a subset of 4 which demonstrated donor alloantigen specific tolerance since they did not reject the C57B1/6 skin. All 4 animals rejected the third party CBA skin, while all 9 Balb/C isografts survived indefinitely. No renal allograft rejection was stimulated by the skin transplants.

To determine whether MB23G2 mAb could reverse acute rejection, seven allografts were performed as described above, but no immunotherapy was administered until day 4. Untreated allografted kidneys demonstrated rejection at this time. The treated animals received MG23G2, 1.5 mg/kg (50 μg) i.v. daily on days 4, 5 and 6 and no further therapy thereafter. Three animals died of ureteric complications in the MG23G2 treated group—the graft histology did not show rejection at the time of death on days 8, 9 and 25. All the animals had their rejection reversed and the remaining 4 survived >60 days with a normal serum creatinine.

Figure 4A:
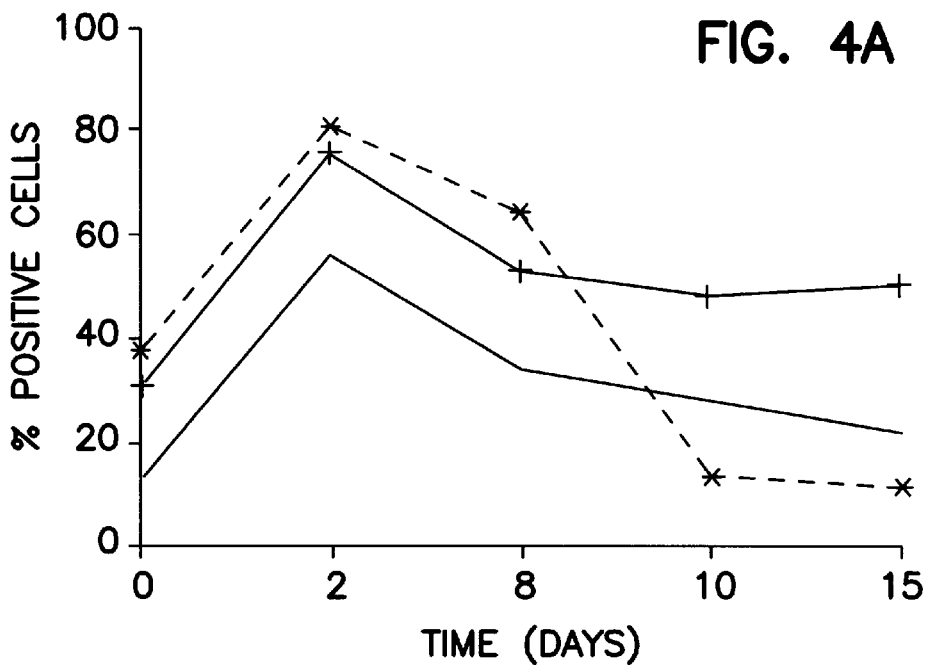
FIG. 4(A–B) shows that MB23G2 binds to circulating T and B lymphocytes but does not decrease the number of circulating lymphocytes.
Figure 4B:
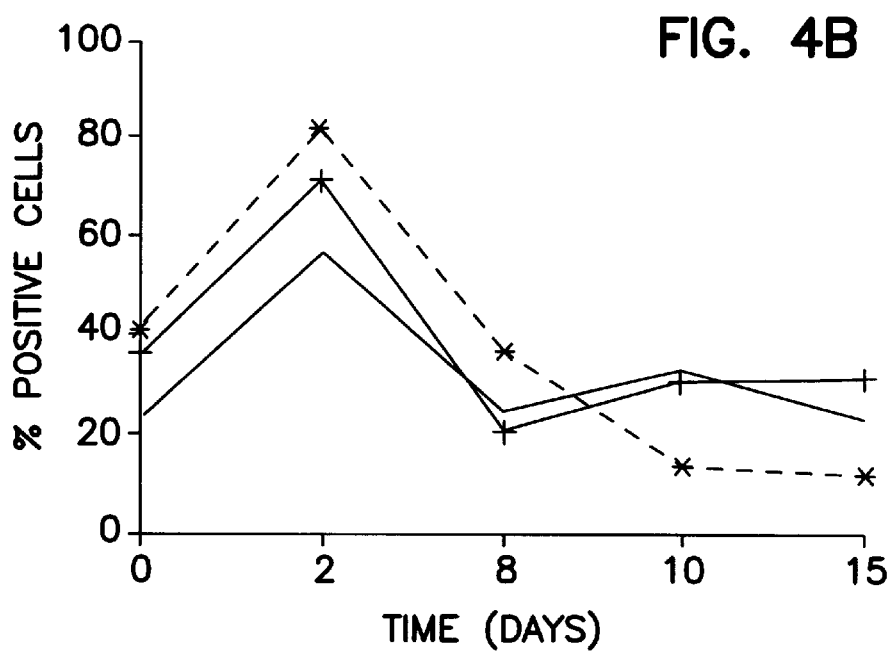

The pharmacologic effects on the peripheral blood of administered MB23G2 in three mice were assessed by giving 30 μg MB23G2 i.v. on two consecutive days using multiparameter FACS analysis. As shown in FIG. 4, MB23G2 bound to the circulating T and B lymphocytes but did not decrease the number of circulating lymphocytes indicating that MB23G2 is a non-depleting antibody. FACS analysis revealed no excess antibody in the plasma by day 8. FACS analysis of the spleen demonstrated that the administered therapy penetrated the lymphoid tissue 24 hours after the second dose of MB23G2.

It is now known to the inventors that MB23G2 binds to a neuraminidase sensitive epitope, while MB4B4 binds to a neuraminidase insensitive epitope. Since CD45 is a protein tyrosine phosphatase, tests were designed to show that allograft tolerance by MB23G2 is related to an alteration in tyrosine phosphorylation of T cell substrates necessary for signal transduction to occur.

EXAMPLE 7

Mechanism of Tolerance Induction by CD45RB Monoclonal Antibody: Differential Inhibition of Tyrosine Phosphorylation of Phospholipase C-γ1

Renal allografts were performed in mice and were induced to survive indefinitely with normal renal function after 2 injections of monoclonal antibody (mAb) to CD45RB (MB23G2, previously designated HB220) while another CD45RB mAb (MB4B4, previously designated HB223) was ineffective. Both mAb are rat IgG2a.

Murine T cell hybridoma A1.1 was stimulated with the CD3 mAb 2C11 in the presence or absence of MB23G2 or MB4B4 mAb. The cells were lysed in SDS, membrane proteins were extracted, run on an SDS polyacrylamide gel and submitted to an immunoblotting procedure. 2C11 mAb induced the tyrosine phosphorylation of multiple substrates. In the presence of M23G2 there was an inhibition of tyrosine phosphorylation of a high molecular weight substrate of an approximate relative molecular mass of 140 kDa. The MB4B4 mAb did not prevent the tyrosine phosphorylation of this substrate. Monoclonal antibody to phospholipase C-γ1 confirmed the identity of this 140 kDa band.

In yet other experiments, use of anti-CD45RB antibodies were found to be effective when administered to primates.

EXAMPLE 8

Prevention of Organ Rejection in Mammals and Reversal of Organ Rejection

Renal allografts were performed on two cynomologous monkeys using a CD45RB monoclonal antibody (which binds to a neuraminidase sensitive epitope), as an immune suppressor and the details are set forth below:
Detailed Experimental Procedures:
1. Animal care:

The animals were housed in the University of Western Ontario primate facility. They are provided with squeeze cages which allow for drug injections and sample collection without having to anesthetize the animal, thereby reducing stress. They were maintained on standard monkey feed, and other foods for diversity. They were allowed regular exercise in the exercise cage. The animal care follows the standard operating procedures for non-human primates provided by veterinary services.

Animals were typed for blood groups. On arrival, the animals were rested for at least 2 weeks. The animals were anesthetized with atropine and ketamine for physical examination, including inspection for oral B virus, TB testing, and de-wormed with Ivernectin 2828. Animals fasted the night prior to any anesthetics.
2. Kidney transplantation:
  1. Donor procedure:

Two donor animals were injected with ketamine, taken to the OR, intubated and put on insofluorane/nitrous oxide. A three stage surgical prep is used. After a midline incision of the two, the left renal artery, vein and ureter were carefully isolated and divided. Grafts were ex-vivo perfused and stored in 4° C. University of Wisconsin solution. The wounds were closed and the animals returned to the cage to recover from the anesthetic. 200–300 ml of saline were given by continuous i.v. during the surgery. During the surgery, the animals were kept warm using a heating lamp, heated saline and heating pad, etc.

Postoperative care followed Standard Operating Procedures. Briefly, the animals remained on a warm water blanket and under a heating lamp for 24 hours. Buprenorphine was given q6h after surgery for 24 hours. The animals were monitored daily. The well recovered donor animals are used as the recipient in future transplantations. The interval between the two surgeries is at least two weeks.
  2. Recipient procedure:

Recipient was anesthetized and prepared preoperatively as described for the donor. After a midline incision, abdominal aorta and inferior vena cava were exposed. End-to-side anastomoses were performed between the donor renal artery and the recipient aorta, as well as between the donor renal vein and the recipient inferior vena cava. The donor ureter was sutured to the recipient's bladder. The right kidney was removed and the wound was closed.
  3. Post-operative care:

The post-operative care is the same as described for the donor. Animals were monitored continually post-operatively for at least 24 hours, more if necessary. They were monitored closely (i.e., several times per day) until feeding and grooming normally. Thereafter, they were monitored at least daily when they received their monoclonal antibody.

Animals were given anti-CD45RB mAb 4 mg IV daily×7 days. The outcome of kidney grafts was measured by percutaneous biopsy weekly and blood creatinine levels twice per week. For these procedures animals were anesthetized with ketamine.

Criteria for early euthanasia would include lethargy, lack of grooming or feeding, significant weight loss (>20%) and renal failure (elevated creatinine levels).

As discussed above, the recipient animals received 4 mg (1 mg/kg) of 6G3-antiCD45RB monoclonal antibody post operatively for 7 days. There were no side effects associated with such infusions. Both animals survived normally until day 16 when each experienced an acute rejection crises. The first animal was euthanized 2 days later on day 18. The second animal was re-treated with 4 mg/kg (16 mg) of 6G3 anti-CD45RB monoclonal antibody. The therapy was given daily by iv for four days. Remarkably the rejection crises completely reversed as the animal was observed to resume normal activities and creatine levels were observed to decrease from a "crises" level of 738 µmol/L to 366 µmol/L. The animal remained well until day 36 when another rejection crises developed. The animal was than euthanized. Histology of the allograft revealed that there was profound endotheliitis on post-operative day 15 just before additional therapy was administered leading to reversal. A biopsy of the allograft of this animal was performed on post-operative day 23 revealing the endotheliitis had cleared.

It is known that control animals will die by day 10 if therapy is not administered in this type of model. (Lazarovits, et al, "A Monoclonal Anti-Act I Reacts with a Late Lymphocyte Activation", KIDNEY INTER. 25:344).

The data suggests two conclusions

[1] Because both monkeys lived past the known date of controls, it is shown the therapy of the invention exhibits significant graft-survival in a primate.

[2] Even more dramatic is the observation that one can reverse acute rejection with anti-CD45RB monoclonal antibodies.

EXAMPLE 9

Additional Monkey Experiments

Two additional cynomolgus monkeys (#3 and #4) have received renal allografts and have been treated with the CD45RB monoclonal antibody 6G3 as the sole form of immunosuppression. Blood grouping was performed to control for ABO compatibility and major histocompatibility complex profiles were obtained using PCR based DNA typing to confirm that allogeneic renal transplants were being performed.

On day 0, a nephrectomy was performed in the recipient animal and the renal allograft was performed. On day seven the second native kidney was removed and from that point on the animal relied on its transplanted kidney. Animals which do not receive immunosuppression or which receive ineffective immunosuppression will reject at a mean of ten days +/- two days (Lazarovits, et al 1984. "A Monoclonal Antibody Anti-Act I Reacts with a Late Lymphocyte activation", KIDNEY INTERN. 25:344).

Monkey #3

This animal was treated with 6G3 antibody 2 mg/kg/day (8 mg)×7 days and then 6 more doses given on Monday, Wednesday and Friday for each of the next two weeks was to be given. Thus 8 mg of 6G3 antibody was planned to be given over three weeks. The animal developed rejection on day 14 and was euthanized.

Monkey #4

This animal received the same therapy as monkey #3. That is 8 mg of 6G3 antibody was given intravenously for 13 doses over three weeks. This animal has done remarkably well and continues to be alive beyond 70 days. No rejection has been diagnosed.

Figure 5:
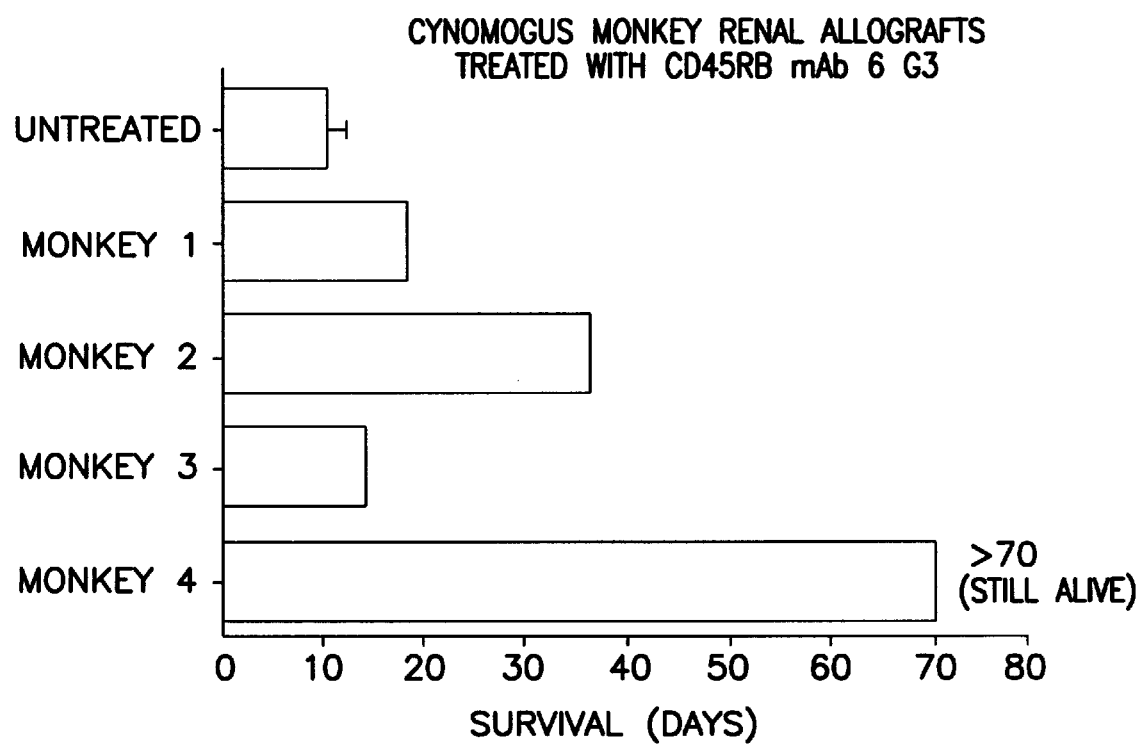
FIG. 5 shows the survival of Cynomolgus monkeys treated with CD45RB in mAb 6G3, after receipt of allografts.

Thus, animals #3 and #4 treated with 6G3 have had significantly prolonged allograft survival which is illustrated in FIG. 5. Monkey #2 of Example 8 is of particular interest because the antibody successfully reversed acute rejection which was predicted by the mouse kidney transplant experiments. Additional experiments are underway to try to determine the cause for relatively early graft failure in monkeys 1 and 3, although both of these animals also had significantly prolonged allograft survival.

EXAMPLE 10

In Vivo Prevention of the Rejection of Heart Transplants

Heterotopic heart transplants from C57B1/6 mice into BALB/C donors were performed essentially as described in R. L. Kirkman et al (1985) Transplantation 40: 719–722. Seven of the mice received 30 µg iv of rat anti-mouse CD45RB monoclonal antibody MB23G2 (HB220) on days 0 and 1 following heart transplantation. Four other mice received 30 µg iv on days 0 and 1 and 100 µg ip of rat anti-mouse CD45RB monoclonal antibody MB23G2 (HB220) daily on days 2 to 11 following heart transplantation. Fourteen control mice received no antibody. Survival of the heterotopic graft was determined by whether the heart was beating and rejection was confirmed by histological analysis. All of the control mice had rejected their hearts by day 14 post-operation, with a mean survival time of 9 days. Mean survival time of the hearts in the group receiving antibody for two days only was 20 days and mean survival time of the hearts in the group receiving antibody for 11 days was 34 days. Table II summarizes the results from this experiment.

TABLE III

MOUSE CARDIAC ALLOGRAFTS

| Groups | Number | Survival (days) | Mean |
|---|---|---|---|
| Untreated | 14 | 8, 8, 9, 9, 9, 9, 9, 9, 9, 10, 11, 11, 11, 14 | 9 |
| CD45RB mAb 30 µg D0, D1 | 7 | 16, 16, 17, 22, 24, 23, 24 | 20 |
| CD45RB mAb 30 µg IV D0, D1 AND 100 µg ip × 9 days | 4 | 15, 30, 38, 38 | 34 |

EXAMPLE 11

In Vivo Prevention of the Rejection of Pancreatic Islet Allograft Transplants

Pancreatic islet allografts were transplanted under the kidney capsule from CBA/J donors into streptozotocin-treated BALB/C recipients essentially as described in M. C. Fabian et al (1993) Transplantation 56: 1137–42. Five control mice received no antibody which eleven mice received 30 µg iv of rat anti-mouse CD45RB monoclonal antibody MB23G2 (HB220) on days 0 to 1 post-operation. Rejection was defined as onset of glycosuria. All islet allografts from control mice had been rejected by day 24 with a mean rejection time of 17 days. Antibody-treated mice showed a mean rejection time of 34 days with two mice having no signs of rejection at day 50 when the experiment was stopped.

Table IV summarizes the result from this experiment.

TABLE IV

MOUSE PANCREATIC ISLET ALLOGRAFTS

| Groups | Number | Survival (days) | Mean |
| --- | --- | --- | --- |
| Untreated | 5 | 12, 12, 15, 24, 20 | 17 |
| CD45RB mAb 0 μg iv D0, D1 | 11 | 23, 32, 20, 30, 30 >50, >50, 21, 23, 47, 50 | 34 |

EXAMPLE 12

In Vivo Treatment of NOD Mice to Inhibit the Onset of Diabetes

Five female NOD mice were treated with 30 μg iv of rat anti-mouse CD45RB monoclonal antibody MB23G2 (HB220) on days 28, 29 and 30 after birth. Five control mice received no antibody treatment. By week 27 all control mice were dead as a result of diabetes. Of the antibody-treated mice 2 died of diabetes while the other 3 remained alive and well until week 35 at which point they were killed and their pancreas examined histologically. There was no sign of insulitis in any of the three surviving animals.

Table V summarizes the results from this experiment.

TABLE V

ONSET OF DIABETES IN NOD MICE

| Groups Diabetes | Number | Survival Without |
| --- | --- | --- |
| Untreated | 5 | 0 (all dead by 27 weeks) |
| CD45RB mAb 30 μg iv days 28, 29, 30 | 5 | 3 > 35 weeks |

Additional experiments have been conducted since this preliminary experiment was conducted. The results are shown in the Table VI below:

TABLE VI

NOD MOUSE SURVIVAL (WEEKS)
Therapy MB23G2 100 ug 2 × week from 2–35 weeks (at which time all remaining mice were euthanized.

| THERAPY | SURVIVAL WEEKS | INSULITIS SCORE* (MEAN) |
| --- | --- | --- |
| MB23G2 (N = 9) | 35 (6), 20 (2), 13 | 0.99 |
| CONTROL (N = 12) | 34 (2), 30 (2), 28, 23 18, 16, 15, 14, 13, 12 | 1.81 |

*Insulitis score obtained from 6 additional animals in each group at 15 weeks.

As seen from the data a significantly greater number of animals survived indefinitely, i.e. until the end of the 35 week experiment compared to the controls. The improvement induced by MB23G2 (HB220 CD45RB mAb) is evident not only in animal survival but also in blood sugar where all of the animals who survived to 35 weeks in the treated group had no evidence of hyperglycemia. This also confirmed by the insulitis score which is a careful histologic assessment of the pancreas. The difference between 1.81 and 0.99 is both biologically and statistically meaningful.

The pharmaceutical utility of the compounds may be additionally shown, for example, in the following in vivo models:

Localized Graft-Versus-Host (GvH) Reaction

In vivo efficacy of the compounds is proven in a suitable animal model, as described, e.g., in Ford et al, TRANSPLANTATION 10 (1970) 258. Spleen cells ($1 \times 10^7$) from 6 week old female Wistar/Furth (WF) rats are injected subcutaneously an day 0 into the left hind-paw of female (F344×WF)F, rats weighing about 100 g. Animals are treated for 4 consecutive days and the popliteal lymph nodes are removed and weighed on day 7. The difference in weight between the two lymph nodes is taken as the parameter for evaluating the reaction.

Kidney Allograft Reaction in Rat

Kidney from a female Fisher 344 rat is transplanted onto the renal vessel of a unilaterally (left side) nephrectomized WF recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the animal is taken as the parameter for a functional graft.

Experimentally Induced Allergic Encephalomyelitis (EAE) in Rats

Efficacy of the Compounds in EAE is measured, e.g., by the procedure described in Levine & Wenk, AMER J PATH 47 (1965) 61; McFarlin et al, J IMMUNOL 113 (1974) 712; Borel, TRANSPLANT. CLIN. IMMUNOL 13(1981)3. EAE is a widely accepted model for multiple sclerosis. Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded.

Freund's Adjuvant Arthritis

Efficacy against experimentally induced arthritis is shown using the procedure described, e.g., in Winter & Nuss, ARTHRITIS & RHEUMATISM 9 (1966) 394; Billingham Davies, HANDBOOK OF EXPERIMENTAL PHARMACOL (Vane & Ferreira Eds, Springer-Verlag, Berlin) 50/II (1979) 108–144. OFA and Wistar rats (male or female, 150 g body weight) are injected, i.e. at the base of the tail or in the hind paw, with 0.1 ml of mineral oil containing 0.6 mg of lyophilized heat-killed Mycobacterium smegmatis. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper. $ED_{50}$ is the oral dose in mg/kg which reduces the swelling (primary or secondary) to half of that of the controls.

Appropriate dosages of the Novel Compounds will of course vary, e.g. depending on the condition to be treated (for example the disease type or the nature of resistance), the, effect desired and the mode of administration.

In general however satisfactory results are obtained on administration parenterally, e.g. intravenously, for example by iv drip or infusion, at dosages on the order of from 0.01 to 2.5 up to 5 mg/kg, e.g. on the order of from 0.05 or 0.1 up to 1.0 mg/kg. Suitable dosages for patients are thus on the order of from 0.5 to 125 up to 250 mg iv, e.g. on the order of from 2.5 to 50 mg iv . The Compounds may be administered daily or every other day or less frequently at diminishing dosages to maintain a minimum level of Compound in the blood during the antigen challenge, e.g., following organ transplant or during the acute phase of an autoimmune disease.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinized blood into the saline at the time of formulation. The presence of an excess of such physiologically inert protein prevents loss of monoclonal antibody or fusion protein by adsorption onto the walls of the container and tubing used with the infusion solution. If albumin is used, a suitable concentration is from 0.5 to 4.50% by weight of the saline solution.

In clinical tests, for example, patients about to undergo kidney, liver or heart transplantation are selected for prophylactic therapy. On the day of transplantation, 2 hours before surgery, a first intravenous infusion of the chimeric CD45RB antibody of Example 2 is administered at a dose of 0.2 mg of each antibody per kg of body weight. Two days after surgery an identical infusion of the antibodies at 0.4 mg/kg of body weight is administered and then repeated at weekly intervals for one month. The intravenous infusions are prepared as follows: the lyophilized antibodies are mixed together and dispersed into 100 ml sterile buffered saline containing 4.51% by weight of human albumin. This saline dispersion is administered to the patients over a 30 minute period. The patients may also receive standard Cyclosporin therapy.

The Compounds are also useful as diagnostic aids, as diagnostic reagents or as components of a diagnostic kit to identify particular sub-populations of leukocytes. The Compounds may be labeled, e.g., fluorolabelled or radiolabelled, using conventional techniques. For example, 25 micrograms of monoclonal antibody in 0.25 ml of 0.12 M sodium phosphate, pH 6.8 is iodinated using 2 mCi $^{125}$I and 10 micrograms chloramine T. After 5 minutes at 23° C., the reaction is stopped by the addition of 20 micrograms of sodium metabisulfite, 3 mg of KI and 1 mg of BSA. Iodinated protein is separated chromatographically. The labeled Compounds are exposed to a frozen tissue section, e.g., from a patient exhibiting symptoms of graft rejection or acute autoimmune disease, exhibiting infiltration of leukocytes. Excess Compound is washed away, and bound Compound is assayed. Substantial binding of the Compounds to leukocytes present in the tissue section suggests that the majority of leukocytes involved are naive rather than memory leukocytes, thereby indicating that therapy with the Compounds and/or with immunosuppressants acting primarily on the T-cell mediated immune response, e.g., Cyclosporin or FK-506, is appropriate.

Finally, the Compounds are useful in a screening assay to identify drugs capable of modulating the biological activity of CD45RB.

Thus, it is apparent that there has been provided, in accordance with the present invention, methods and products which will substantially benefit those with autoimmune diseases and those receiving organ transplants. While the invention has been described in conjunction with specific embodiments thereof, it is evident that many modifications and variations will be apparent to those skilled in the art.

For instance the CD45RB epitope is now known to be 190KDA. Isolation of the epitope and compounds binding to the epitope are contemplated by this invention.

Accordingly, it is intended to include all such alternatives, modifications and variations set forth within the spirit and scope of the appended claims.

What is claimed is:

1. A pharmaceutical composition comprising an amount of a monoclonal antibody, a fragment thereof or a mixture thereof that specifically binds to the CD45RB epitope of the CD45RB isoform of the leukocyte common antigen, wherein said amount is effective to inhibit a T-cell mediated immune response in a recipient to a tissue or organ transplant.

2. A pharmaceutical composition, comprising an amount of a monoclonal antibody, a fragment thereof or a mixture thereof which specifically binds to the CD45RB epitope of the CD45RB isoform of the leukocyte common antigen, wherein said amount is effective to inhibit a T-cell mediated immune response in an animal having an autoimmune disease.

3. The pharmaceutical composition of claim 1 or 2 which comprises an anti-CD45RB monoclonal antibody.

4. The pharmaceutical composition of claim 1 wherein the recipient is a human.

5. The pharmaceutical composition of claim 2 wherein the animal is a human.

6. The pharmaceutical composition of claim 1 wherein the amount is effective to induce immune tolerance in the recipient to the transplant.

7. The pharmaceutical composition of claim 1, wherein said tissue or organ transplant is allogeneic to the recipient.

8. The pharmaceutical composition of claim 2 wherein the autoimmune disease is inflammatory bowel disease, multiple sclerosis, Type I diabetes, systemic lupus erythematosus or rheumatoid arthritis.

9. The pharmaceutical composition of claims 1 or 2 which is adapted for parenteral administration.

10. The pharmaceutical composition of claim 9, which is adapted for intravenous administration.

11. The pharmaceutical composition of claims 1 or 2, which comprises an aqueous carrier.

12. The pharmaceutical composition of claim 11 wherein the carrier is sterile water.

13. The pharmaceutical composition of claim 11 wherein the carrier is buffered physiological saline.

14. The pharmaceutical composition of claim 13 which further comprises human serum albumin.

15. The pharmaceutical amount of claims 1 or 2 wherein the composition provides a dose of 0.01–5 mg/kg of said monoclonal antibody, said fragment thereof or said mixture thereof.

16. The pharmaceutical composition of claims 1 or 2 which comprises 0.5–250 mg of said monoclonal antibody, said fragment thereof or said mixture thereof.

* * * * *

UNITED STATES PATENT AND TRADEMARK OFFICE
CERTIFICATE OF CORRECTION

PATENT NO.: 6,099,838
DATED: August 8, 2000
INVENTOR(S): Lazarovits et al.

It is certified that error appears in the above-identified patent and that said Letters Patent is hereby corrected as shown below:

In column 6, lines 4-5, insert a paragraph break after "source.".

In column 6, line 5, delete "obviously" and insert --Obviously--, therefor.

In column 11, line 58, delete "day S" and insert --day 5--, therefor.

In column 20, line 52, delete "amount" and insert --composition--, therefor.

In column 20, line 53, delete "composition provides a dose of 0.01-5" and insert --amount provides 0.01-5--, therefor.

Signed and Sealed this

Seventeenth Day of April, 2001

*Attest:*

NICHOLAS P. GODICI

*Attesting Officer*     *Acting Director of the United States Patent and Trademark Office*